United States Patent [19]

Nwaneri et al.

[11] Patent Number: 5,242,429

[45] Date of Patent: Sep. 7, 1993

[54] ENTERAL FEEDING TUBE WITH GUIDE WIRE

[76] Inventors: Ngozika J. Nwaneri, 7214 Kempton Rd., Lanham, Md. 20706; Leonard D. Amalaha, 4922 St. Elmo Ave., Bethesda, Md. 20814

[21] Appl. No.: 882,964

[22] Filed: May 14, 1992

[51] Int. Cl.⁵ .................... A61M 31/00; A61M 5/178; A61M 25/00
[52] U.S. Cl. .................................. 604/270; 604/170; 604/282
[58] Field of Search ............... 604/164, 170, 264, 270, 604/280, 282

[56] References Cited

U.S. PATENT DOCUMENTS

| | | | |
|---|---|---|---|
| 1,899,781 | 2/1933 | Twiss | 604/270 |
| 3,189,031 | 6/1965 | Andersen | 604/270 |
| 4,490,143 | 12/1984 | Quinn et al. | |
| 4,516,970 | 5/1985 | Kaufman et al. | 604/270 |
| 4,655,214 | 4/1987 | Linder | |
| 4,659,328 | 4/1987 | Potter et al. | 604/170 |
| 4,692,152 | 9/1987 | Emde | |
| 4,781,704 | 11/1988 | Potter | 604/270 |
| 4,838,873 | 6/1989 | Landskron et al. | |
| 4,850,983 | 7/1989 | Brenneman et al. | 604/270 |
| 4,874,365 | 10/1989 | Frederick | |
| 5,034,387 | 8/1991 | Quinn | |
| 5,085,216 | 2/1992 | Henley, Jr. et al. | 128/636 |
| 5,092,847 | 3/1992 | Pozzo | 604/170 |

Primary Examiner—John D. Yasko
Assistant Examiner—Adam J. Cermak
Attorney, Agent, or Firm—Richard C. Litman

[57] ABSTRACT

An enteral feeding device for the admission of fluids into a patient. The device includes a female proximal end connector, a flexible feeding tube, a fluid discharge tube, and a probe, respectively, joined axially to provide a diametrically uniformed outer periphery the entire length of the enteral feeding tube. The guide wire has a male proximal end connector affixed to the proximal end thereof and a coiled helical spring immovably attached to the distal end thereof. An annular stop flange is located interiorly adjacent the proximal end of the fluid discharge chamber which restricts the axial movement of the guide wire when inserted into the enteral feeding tube. A plurality of fluid discharge orifices are radially disposed equidistantly apart around the outer periphery of the fluid discharge chamber. A concave slope is interiorly located juxtaposed the bottom surface of the fluid discharge chamber. The combination of the radially disposed fluid discharge orifices and the concave slope provide an efficient distribution of fluid from the enteral feeding tube. A plurality of stabilization weights are interposed within the probe. The arrangement of stabilization weights combined with the radial distribution of the fluid provides greater stability of the probe during slight movements of the patient. Further, a thermometer-shaped rigid bolus tip is located on the distal end of the probe.

8 Claims, 1 Drawing Sheet

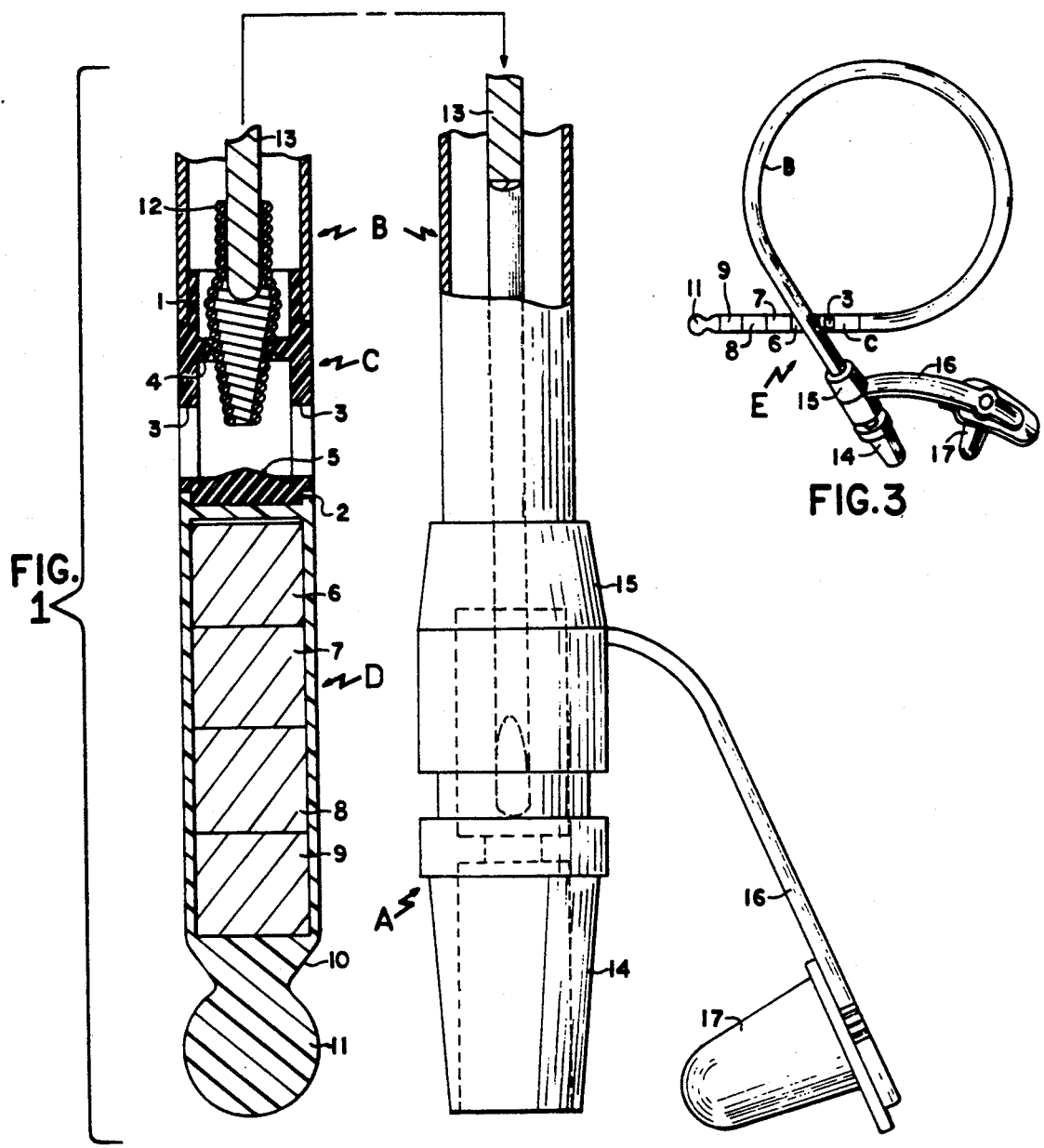
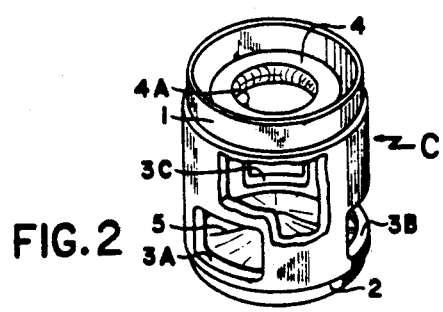
FIG. 1
FIG. 2
FIG. 3

ENTERAL FEEDING TUBE WITH GUIDE WIRE

BACKGROUND OF THE INVENTION

1. Field of the Invention

The present invention relates to an enteral feeding tube for enteric feeding or for administering fluids to a patient.

2. Description of Prior Art

The treatment of a patient who can not or who refuses to voluntarily ingest often requires enteric therapy. It is rudimentary practice throughout the medical community to administer nutritional and other prescribed fluids to patients through an intubating device commonly referred to as an enteral feeding tube. A guide wire or stylet is inserted into the enteral feeding tube prior to inserting the enteral feeding tube into the patient. With the guide wire contained within the enteral feeding tube, the enteral feeding tube can be guided within the patient to a desired position. A probe, having a rigid bolus tip adjacent the distal end of the enteral feeding tube, assists in the insertion of the enteral feeding tube into the patient. The probe further aids in the stabilization of the enteral feeding tube once positioned within the patient. Conventional configurations of enteral feeding tubes normally employ probes having a pointed bolus, a rounded bolus, or a test tube shaped bolus, each configured to facilitate the insertion of the enteral feeding tube within the patient and the withdrawal of the enteral feeding tube from the patient without invoking internal injury to the patient. However, internal injury is still prosaic in the administration of enteral feeding tubes. An enteral feeding tube having a probe with an improved bolus tip, such as a thermometer-shaped rigid bolus tip, would promote the reduction of internal injury to patients.

Enteral feeding tubes are available and widely used in medical practice, nonetheless, no such enteral feeding tube is configured with a thermometer-shaped rigid bolus tip.

U.S. Pat. No. 5,034,387 issued Aug. 6, 1991 to David G. Quinn discloses an improved enteral feeding tube and the improved placement thereof within the body.

U.S. Pat. No. 4,874,365 issued Oct. 17, 1989 to Warren P. Frederick shows a naso-gastic feeding tube and a method of positioning the tube within the patient.

U.S. Pat. No. 4,838,873 issued Jun. 13, 1989 to Jurgen Landskron et al. discloses an apparatus for introducing liquids and/or elongated elements into a body cavity.

U.S. Pat. No. 4,692,152 issued Sep. 8, 1987 to Carsten Emde discloses a medical probe or tube suitable for enteral feeding having a substantially teardrop-shaped bolus.

U.S. Pat. No. 4,655,214 issued Apr. 7, 1987 to Gerald S. Linder shows an improved apparatus and method for the intubation of catheters.

U.S. Pat. No. 4,490,143 issued Dec. 25, 1984 to David G. Quinn et al. discloses a feeding assembly for the internal admission of fluids to a patient comprising a tube having a rigid bolus near its distal end to facilitate the peristaltic movement of the assembly during insertion.

None of the above patents, taken either singly or in combination, is seen to describe the instant invention as claimed.

SUMMARY OF THE INVENTION

The present invention relates to an enteral feeding tube for the admission of fluids to a patient. The enteral feeding tube basically comprises a female proximal end connector, a flexible feeding tube, a fluid discharge chamber, and a probe, respectively, connected axially in series to provide a device having substantially a diametrically uniformed outer surface. A cap plug is joined to the female proximal end connector by an integral strap. The fluid discharge chamber includes a plurality of fluid discharge orifices radially disposed equidistantly around the outer periphery of the fluid discharge chamber and further includes a concave slope located interiorly adjacent the bottom surface or the distal end of the fluid discharge chamber. This combination of the radially disposed plurality fluid discharge orifices and the concave slope provides an efficient radial discharge of the fluid from the enteral feeding tube. A plurality of stabilization weights are interposed within the probe. The combination of the radial discharge of the fluid provided by the configuration of the fluid discharge chamber and the plurality of stabilization weights contained within the probe enhances the stability of the device during slight movements of the patient. A thermometer-shaped rigid bolus tip is located at the distal end of the probe. The thermometer-shaped rigid bolus tip includes a spherical member integrally attached to a tapered end of a frustoconical shaped neck. The frustoconical shaped neck is in turn joined to the portion of the probe containing the plurality of stabilization weights. This thermometer-shaped rigid bolus tip offers a low coefficient of friction as does the diametrically uniformed surface of the enteral feeding tube. This low coefficient of friction provides optimum ease of the insertion of the device into the patient. A male proximal end connector is attached to the proximal end of the guide wire and a coiled helical spring is fixed to the distal end of the guide wire. The coiled helical spring along with the guide wire is removably inserted into and through the female proximal end connector, into and through the flexible feeding tube, and further into the proximal end of the fluid discharge chamber. An annular stop flange is located interiorly adjacent the proximal end of the fluid discharge chamber. This annular stop flange provides a seat for the engagement of the coiled helical spring, thus restricting the axial movement of the coiled helical spring and preventing the guide wire from communicating with and exiting through any one of the plurality of fluid discharge orifices. This reduces the risk of causing internal tissue damage to a patient.

Accordingly, one object of the present invention is to provide an enteral feeding tube which yields an efficient radial discharge of fluid.

Another object of the present invention is to provide an enteral feeding tube which offers enhanced stabilization of the probe during slight movements of the patient.

Another object of the invention is to provide an enteral feeding tube which imparts optimum ease in inserting the enteral feeding tube into and within the patient.

A further object of the present invention is to provide a enteral feeding tube which ensures an engagement of the guide wire which reduces the risk of the guide wire causing internal injury to the patient.

These and other objects of the present invention will become readily apparent upon further review of the following specification and drawings.

BRIEF DESCRIPTION OF THE DRAWINGS

FIG. 1 is a partially cutaway side elevational view of the present invention;

FIG. 2 is a perspective view of the present invention; and

FIG. 3 is a partially cutaway perspective view of the fluid discharge chamber.

Similar reference characters denote corresponding features consistently throughout the attached drawings.

DETAILED DESCRIPTION OF THE PREFERRED EMBODIMENT

Now referring to the drawing and more particular, to FIG. 1 which shows a male proximal end connector 14 rigidly connected to a guide wire 13. The guide wire 13, preferably constructed of stainless steel, provides firm support for the relatively soft flexible feeding tube B during the insertion of the enteral feeding tube E into the patient. The distal end of the female proximal end connector 15 is fixed to the proximal end of the flexible feeding tube B, such as by a heat setting technique, ultrasonic welding, or a resin type bonding agent. The integral strap 16 joins the cap plug 17 to the female proximal end connector 15. When the distal end of the male proximal end connector 14 is mated with the proximal end of the female proximal end connector 15, the cap plug 17 fits into the proximal end of the male proximal end connector 14, hence providing temporary rigidity.

The fluid discharge chamber C has a beveled edge 1 adjacent the proximal end thereof. The outer diameter of the beveled edge 1 mates with the inner diameter of the distal end of the flexible feeding tube B to provide a tight fit configuration. This mating of the flexible feeding tube B and the fluid discharge chamber C provides a diametrically uniformed outer surface. The flexible feeding tube B and the fluid discharge chamber C are joined together by a heat setting technique, ultra sonic welding, or the like. An annular stop flange 4 is integrally formed to the inner surface of the fluid discharge chamber C adjacent the proximal end thereof. The annular stop flange 4 provides a restrictive fit for the coiled helical spring 12 attached to the distal end of the guide wire 13. This annular stop flange 4 restricts the axial movement of the coiled helical spring 12 and the guide wire 13 and prevents the coiled helical spring 12 along with the guide wire 13 from communicating with or passing through any one of the plurality of fluid discharge orifices 3. This reduces the risk of potential injury to the patient. The internal bottom surface adjacent the distal end of the fluid discharge chamber C is contoured to provide a concave slope 5 which facilitates in the complete and timely radial discharge of fluid from the fluid discharge chamber C through the plurality of fluid discharge orifices 3. The outer distal end of the fluid discharge chamber C includes a beveled edge 2. The outer diameter of this beveled edge 2 mates with the inner diameter of the proximal end of the probe D to provide tight fit configuration. This mating of the fluid discharge chamber C and the probe D provides a diametrically uniformed outer surface. The fluid discharge chamber C is permanently and rigidly conjugated to the probe D in a manner such as heat setting, ultrasonic welding, or through a resin bonding agent. The four stabilization weights 6,7,8 and 9 or any number of stabilization weights for that matter, are embedded in the cavity of the probe D to provide a snug fit arrangement. The distal end of the probe D is configured into a thermometer-shaped rigid bolus tip 11 having a spherical member integrally attached to the tapered end of a frustoconical-shaped neck 10 which is in turn joined to the portion of the probe D juxtaposed the plurality of stabilization weights 6,7,8 and 9. The thermometer-shaped rigid bolus tip 11 has an outer diameter substantially equal to the outer diameter of the rest of the probe D, the fluid discharge chamber C, and the flexible feeding tube B. This arrangement provides greater ease in inserting the enteral feeding tube E into the patient and in withdrawing the enteral feeding tube E from the patient. The contour of the thermometer-shaped rigid bolus tip 11 also greatly reduces the risk of injury to a patient.

Now, referring to FIGS. 1 and 2, the fluid discharge chamber C has a radial cylindrical profile having a beveled edge 1 adjacent the proximal end thereof purposed to link with the distal end of the flexible feeding tube B to form a permanent bond as was prescribed above. There exists an internal annular stop flange 4 integrally attached adjacent the proximal end of the fluid discharge chamber C for the purpose of steadying or controlling a coiled helical spring 12 attached to the distal end of guide wire 13. This annular stop flange 4 prevents the coiled helical spring 12 and the guide wire 13 from communicating with and passing through the fluid discharge orifices 3A, 3B, 3C (shown in FIG. 2) and consequently causing injury to a patients internal tissues. The fluid discharge orifices 3A, 3B, 3C are radially oriented equidistantly apart adjacent the distal end of the fluid discharge chamber C. This provides a three dimensional fluid discharge pattern. This three dimensional fluid discharge pattern in combination with the stabilization weights 6,7,8 and 9 interposed within the probe D provide greater stability of the probe D during slight movements of the patient. Entry of the fluid through the flexible feeding tube B into the fluid discharge chamber C is through the radial opening 4A of the annular stop flange 4, which has a diameter smaller than that of the tapered coiled helical spring 12. The purpose of permanently bonding the proximal end of the fluid discharge chamber C to the distal end of the flexible feeding tube B and permanently bonding the distal end of the fluid discharge chamber C to the proximal end of the probe D in the manner revealed above is to provide a diametrically uniformed surface along the entire length of the enteral feeding tube E. This is to offer lower frictional coefficient and thus, provide a greater ease of insertion and withdrawal of the enteral feeding tube E. The concave slope 5 adjacent the inner bottom surface of the fluid discharge chamber C ensures the efficient distribution of the fluid through the fluid discharge orifices 3A, 3B, 3C.

Finally, referring to FIG. 3, the enteral feeding tube E is shown in its entirety. The enteral feeding tube E includes a female proximal end connector 15, a flexible feeding tube B, a fluid discharge chamber C, and a probe D connected axially in series to provide an enteral feeding tube having a diametrically uniformed outer periphery. An integral strap 16 couples a cap plug 17 to the female proximal end connector 15. The distal end of the female proximal end connector 15 is joined by the flexible feeding tube B to the proximal end of the fluid discharge chamber C. A plurality of openings or a plurality of fluid discharge orifices 3 are radially disposed adjacent the distal end of the fluid discharge chamber C to provide a radial discharge of fluid therefrom. The distal end of the fluid discharge chamber C is further connected to the proximal end of the probe D. The probe D includes a plurality of stabilization weights 6,7,8 and 9 interposed therein. These stabilization weights 6,7,8 and 9 can be of lead, mercury, or any suitable material. The probe D also includes a thermometer-shaped rigid bolus tip 11 adjacent the distal end thereof.

The enteral feeding tube E is predominantly fabricated of a plastic material, with the exception of the plurality of stabilization weights 6,7,8 and 9. The probe D in particular should be formed of a material which resists the affects of the hydrochloric acid within the stomach.

It is to be understood that the present invention is not limited to the sole embodiment described above, but encompasses any and all embodiments within the scope of the following claims.

We claim:

1. An enteral feeding device for administering fluid into a stomach of a patient, said device comprising:
   (a) a female proximal end connector;
   (b) a flexible feeding tube being connected to said female proximal and connector;
   (c) a fluid discharge chamber having a means to discharge said fluid radially adjacent a distal end thereof and having flange means interiorly located adjacent a proximal end thereof, said fluid discharge chamber being connected to said flexible feeding tube;
   (d) a probe having a rigid bolus tip located at a distal end, a means to stabilize said probe contained within said probe, said probe being connected to said fluid discharge chamber; and
   (e) a guide wire having a male proximal end connector attached adjacent a proximal end thereof and having a coiled helical spring fixed to a distal end thereof, said guide wire being removably inserted into and through said female proximal end connector and said flexible feeding tube, and into a proximal end of said fluid discharge chamber, said coiled helical spring engaging with said annular flange means within said fluid discharge chamber, and said male and female proximal end connectors engaging to rigidly secure said guide wire within said enteral feeding tube, whereby said enteral feeding tube is inserted into the patient and is guided to a desired position by manipulating said probe by said guide wire and once positioned fluid is permitted to pass through said device and be discharged within said patient through said fluid discharge chamber.

2. The device according to claim 1, further comprising a diametrically uniformed outer periphery formed by a connection of said probe, said fluid discharge chamber, and said flexible feeding tube, respectively, whereby said diametrically uniformed outer periphery has a low coefficient of friction, thus providing greater ease in inserting said device within the patient.

3. The device according to claim 1, further comprising a plurality of stabilization weights forming said means to stabilize said probe, whereby said means to stabilize said probe compensates for movement of the patient such that the position of the device is substantially maintained.

4. The device according to claim 1, further comprising a thermometer-shaped rigid bolus tip including a spherical member, a frustoconical-shaped neck having a tapered end and an opposite end joined to a portion of said probe containing the means to stabilize said probe, the spherical member joined to the tapered end, whereby said spherical section in combination with said tapered end produces a low coefficient of friction, thus providing greater ease in inserting said device within the patient.

5. The device according to claim 1, further comprising a plurality of fluid discharge orifices radially disposed adjacent said distal end and spaced equidistantly apart around an outer periphery of said fluid discharge chamber forming said means to discharge said fluid, whereby the fluid is discharged radially through said plurality of fluid discharge orifices.

6. The device according to claim 1, further comprising a concave sloped surface interiorly located adjacent said distal end of said fluid discharge chamber, whereby the fluid is directed radially within said fluid discharge chamber along said concave slope.

7. The device according to claim 1, wherein said annular flange means comprises an annular stop flange being located interiorly of said proximal end of said fluid discharge chamber providing a seat means to provide a seat for said guide wire in the upper portion of said fluid discharge chamber, whereby said annular stop flange restricts the axial movement of said guide wire from entering into said distal end of said fluid discharge chamber, thus preventing said guide wire from communicating with and passing through any one of said plurality of fluid discharge orifices.

8. An enteral feeding device for the administering of fluid into a stomach of a patient, said device comprising:
   (a) a female proximal end connector;
   (b) a flexible feeding tube being fixed to said female proximal end connector;
   (c) a fluid discharge chamber including an annular stop flange being interiorly located adjacent a proximal end thereof, a plurality of fluid discharge orifices being radially disposed equidistantly apart adjacent an outer surface of a distal end thereof, and a contoured bottom surface being concave in slope interiorly located adjacent said distal end, said fluid discharge chamber being fixed to said flexible feeding tube to provide a diametrically uniformed outer periphery;
   (d) a probe having a thermometer-shaped rigid bolus tip located at a distal end thereof and a plurality of weights being interposed therein, said probe being connected to said fluid discharge tube to further provide said diametrically uniformed outer periphery; and
   (e) a guide wire including a male proximal end connector adjacent a proximal end thereof and a coiled helical spring fixed to a distal end thereof, said guide wire being removably inserted into and through said female proximal end connector and said flexible feeding tube, and into said proximal end of said fluid discharge chamber where said coiled helical spring engages with said annular stop flange, said male and female proximal end connectors mate to secure said guide wire within said enteral feeding tube, whereby said enteral feeding tube is inserted into the patient and is guided to a desired position by manipulating said probe by said guide wire and once positioned fluid is permitted to pass through said device and be discharged radially within said patient through said fluid discharge chamber, and further said diametrically uniformed outer periphery provides a low coefficient of friction, thus providing greater ease for inserting said device within the patient.

* * * * *